(12) United States Patent
Neoh

(10) Patent No.: US 10,071,026 B2
(45) Date of Patent: Sep. 11, 2018

(54) LOW PROFILE GASTROSTOMY TUBES

(71) Applicant: Cook Medical Technologies LLC, Bloomington, IN (US)

(72) Inventor: Wen Hong Neoh, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 13/897,630

(22) Filed: May 20, 2013

(65) Prior Publication Data

US 2013/0317473 A1 Nov. 28, 2013

Related U.S. Application Data

(60) Provisional application No. 61/651,691, filed on May 25, 2012.

(51) Int. Cl.
*A61J 15/00* (2006.01)
*A61M 39/10* (2006.01)
*A61J 1/20* (2006.01)

(52) U.S. Cl.
CPC ......... *A61J 15/0015* (2013.01); *A61J 15/003* (2013.01); *A61J 15/0026* (2013.01);
(Continued)

(58) Field of Classification Search
CPC .... A61M 25/02; A61M 25/04; A61M 39/223; A61M 39/26; A61M 39/1055;
(Continued)

(56) References Cited

U.S. PATENT DOCUMENTS 1,430,313 A 9/1922 Millity
2,120,510 A 6/1938 Rhoads
(Continued)

FOREIGN PATENT DOCUMENTS

EP 0 853 937 A1 7/1998
EP 2 422 828 A1 2/2012

OTHER PUBLICATIONS

Extended European Search Report for European Application No. 13168145.4 dated Oct. 9, 2014.

*Primary Examiner* — Shefali Patel
(74) *Attorney, Agent, or Firm* — Brinks Gilson & Lione

(57) ABSTRACT

Devices, systems and methods for delivering nutrients to a patient are provided. A gastrostomy feeding device includes a device housing having a proximal portion having an opening therein, a channel operably connected to the opening in the proximal portion, a distal portion having an opening therein, a lumen operably connected to the opening in the distal portion, and a cavity formed within the device housing. The device also includes a rotatable member positioned completely within the cavity and that is rotatable within the cavity relative to the housing. The rotatable member includes a first opening and a second opening and a lumen extending therebetween. The rotatable member is rotatable from a closed configuration to an open configuration where the second opening of the rotatable member is operably connected to the lumen of the device housing. The device further includes an expandable member positioned on the distal portion.

17 Claims, 8 Drawing Sheets

(52) U.S. Cl.
CPC ....... *A61J 15/0046* (2013.01); *A61J 15/0092* (2013.01); *A61M 39/1055* (2013.01); *A61J 1/2051* (2015.05); *A61J 1/2096* (2013.01); *A61J 15/0049* (2013.01)

(58) Field of Classification Search
CPC .... A61J 15/00; A61J 15/0011; A61J 15/0015; A61J 15/0026; A61J 15/003; A61J 15/0042; A61J 15/0049; A61J 15/0092; A61J 15/0046
USPC ....... 604/104, 174, 175, 246, 248, 533, 535; 251/149.2
See application file for complete search history.

(56) References Cited

U.S. PATENT DOCUMENTS

| | | | |
|---|---|---|---|
| 3,078,068 A * | 2/1963 | Romney | ............. 251/149.2 |
| 3,618,892 A * | 11/1971 | Sciuto, Jr. | ............. 251/149.2 |
| 3,961,632 A | 6/1976 | Moossun | |
| 4,809,694 A | 3/1989 | Ferrara | |
| 5,326,072 A * | 7/1994 | Wuthrich | ........ F16L 37/47 137/616.7 |
| 5,584,847 A | 12/1996 | Duluco et al. | |
| 5,681,027 A * | 10/1997 | Wuethrich | ........ F16L 37/47 137/616.7 |
| 5,716,347 A | 2/1998 | Gibbs et al. | |
| 5,746,717 A | 5/1998 | Aigner | |
| 5,836,924 A * | 11/1998 | Kelliher | ........ A61J 15/0015 604/104 |
| 5,919,420 A | 7/1999 | Niermann et al. | |
| 6,872,189 B2 | 3/2005 | DeLegge | |
| 7,063,685 B2 | 6/2006 | Rome | |
| 7,628,775 B2 | 12/2009 | Adams et al. | |
| 7,766,877 B1 | 8/2010 | Watson et al. | |
| 2003/0212385 A1 | 11/2003 | Brenner et al. | |
| 2004/0082909 A1 | 4/2004 | Shia et al. | |
| 2005/0004540 A1* | 1/2005 | McNally | ........ A61J 15/0015 604/332 |
| 2005/0124932 A1 | 6/2005 | Foster et al. | |
| 2009/0192465 A1 | 7/2009 | Smith | |
| 2010/0280489 A1 | 11/2010 | Nishtala et al. | |

* cited by examiner

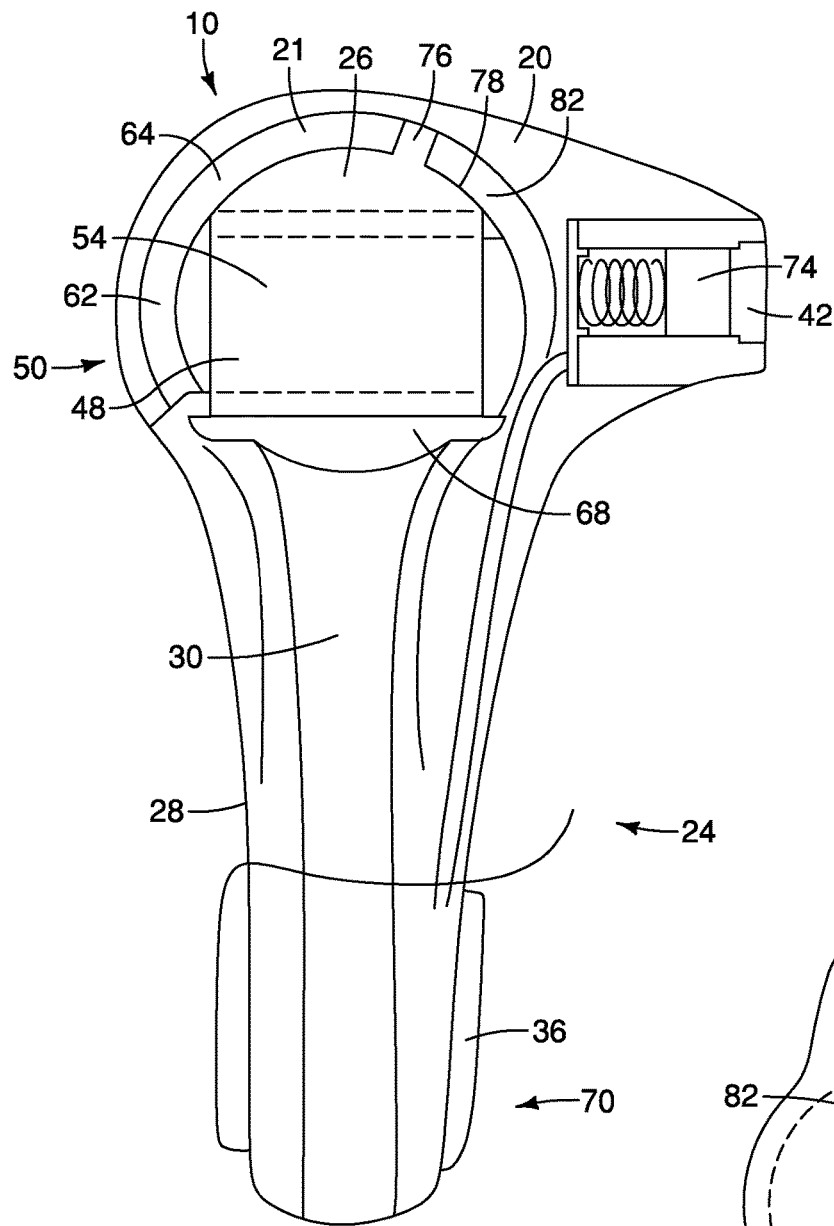
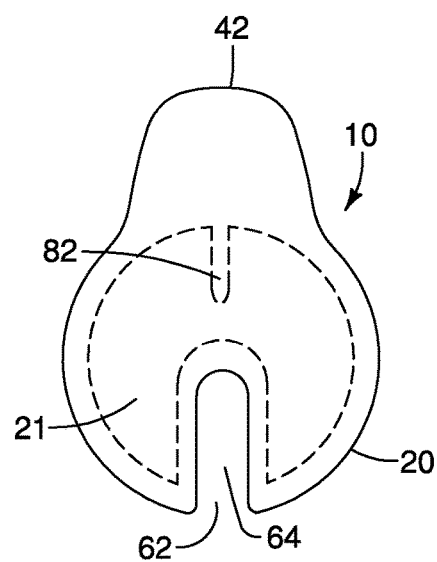
FIG. 2
FIG. 3

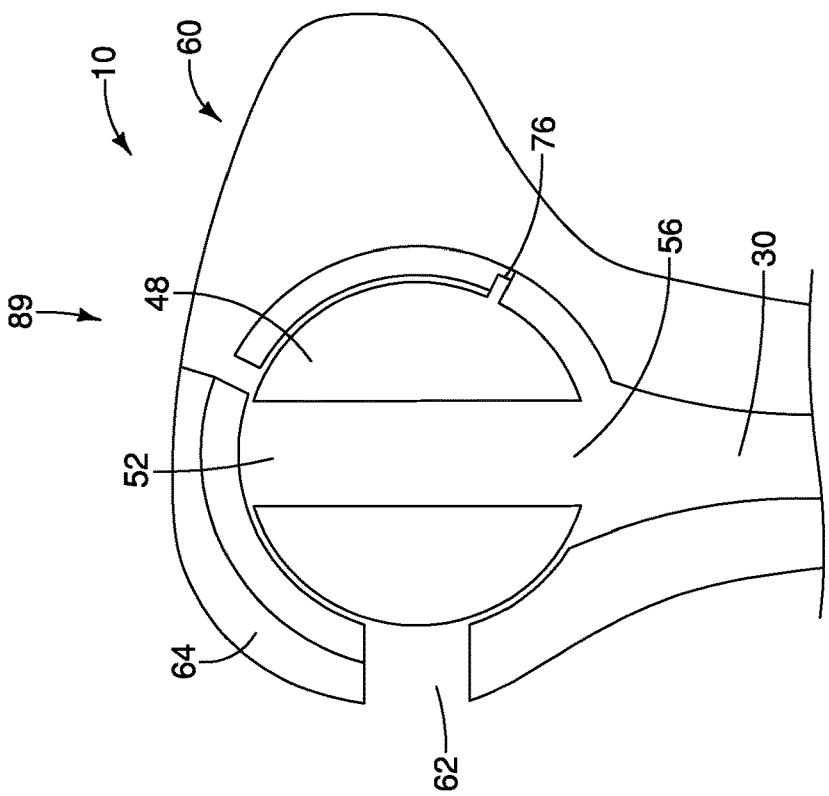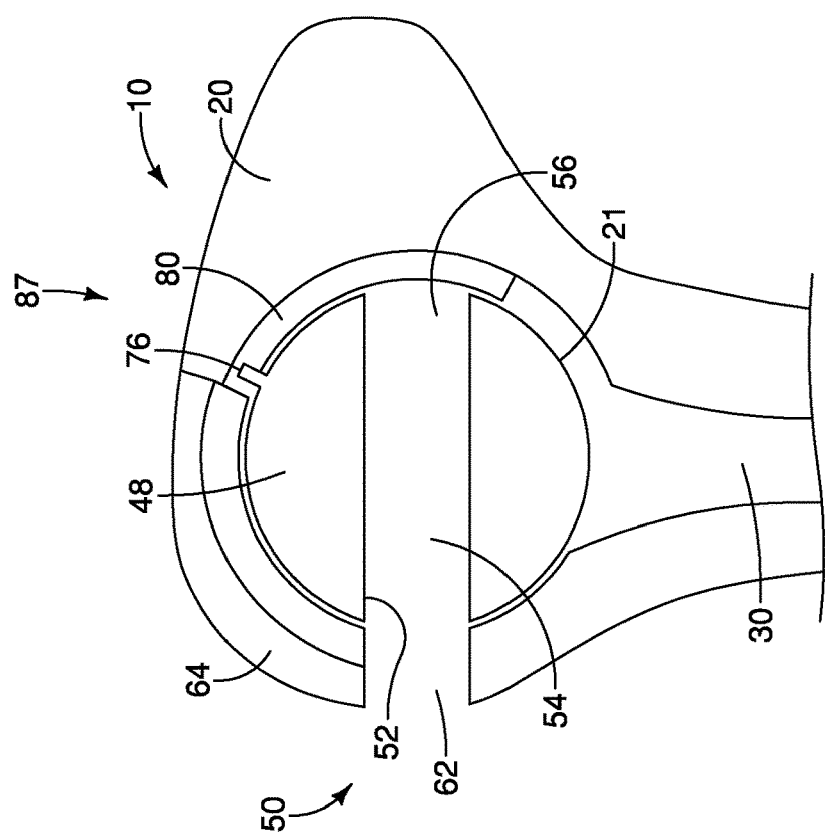

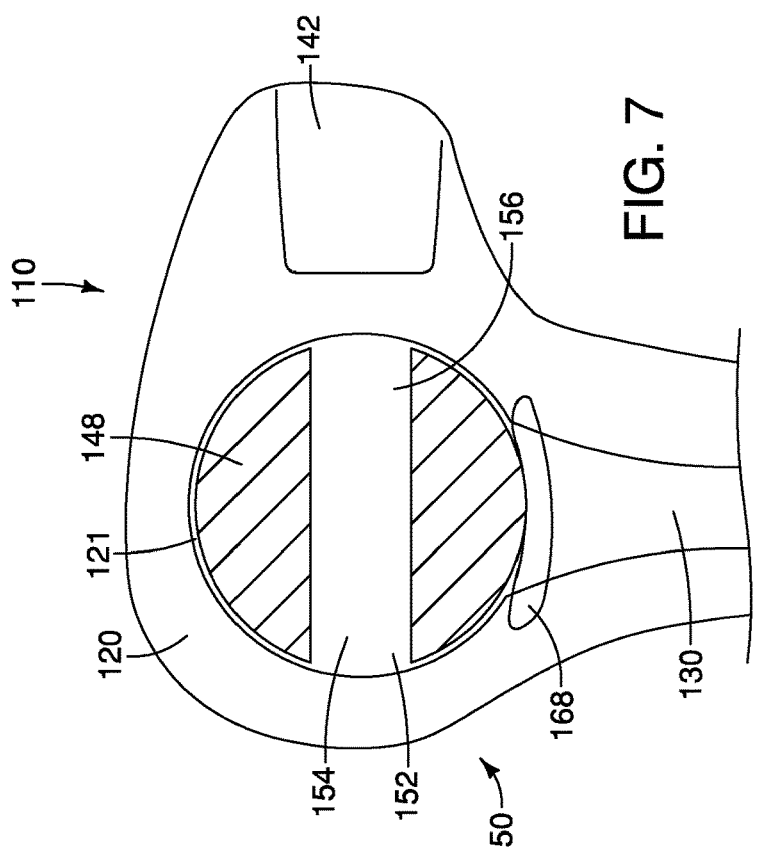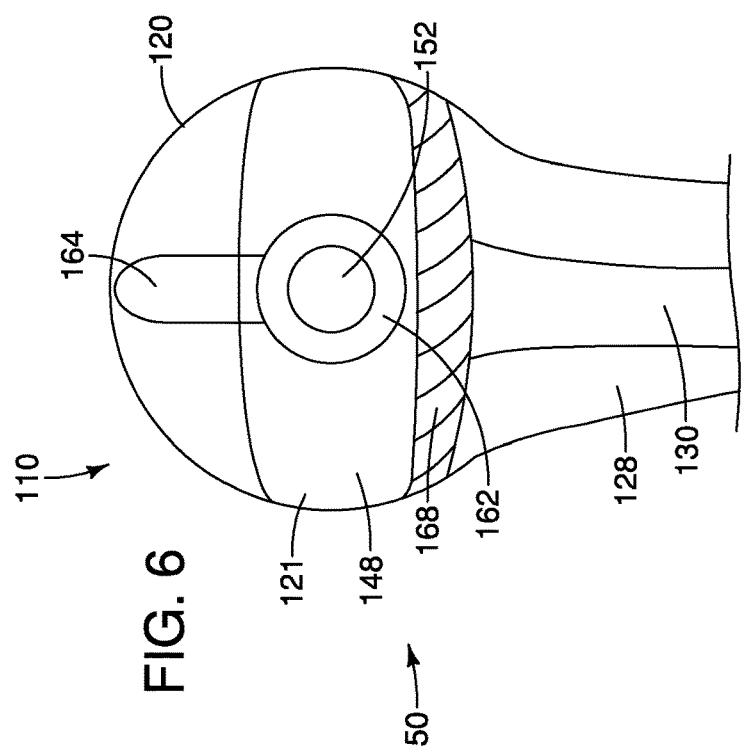

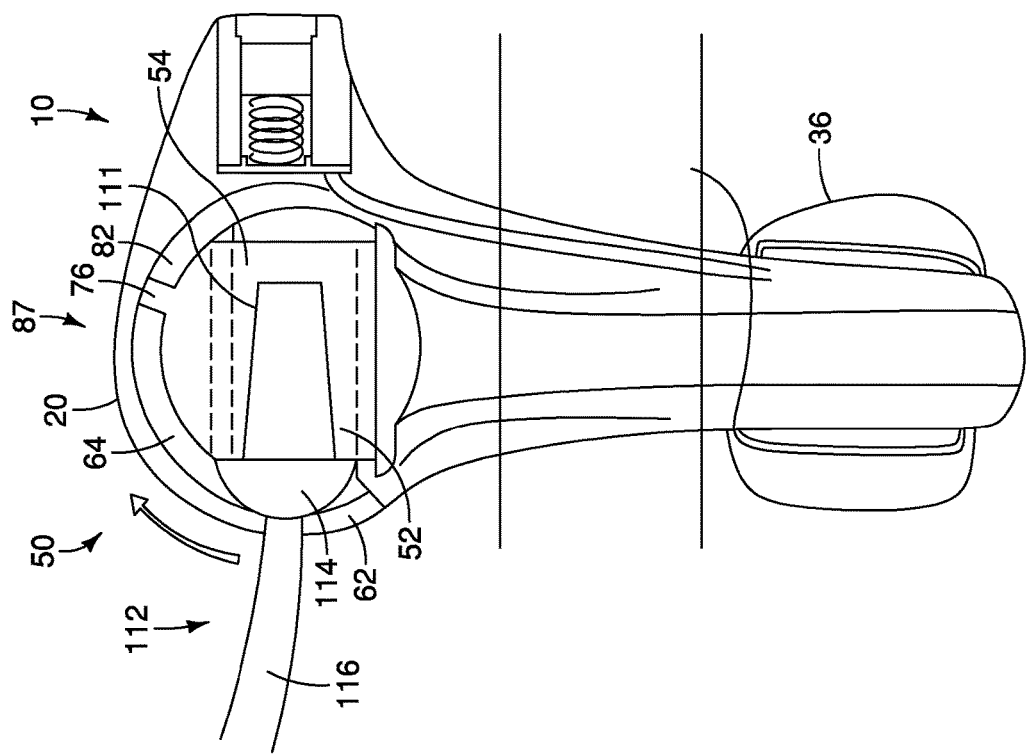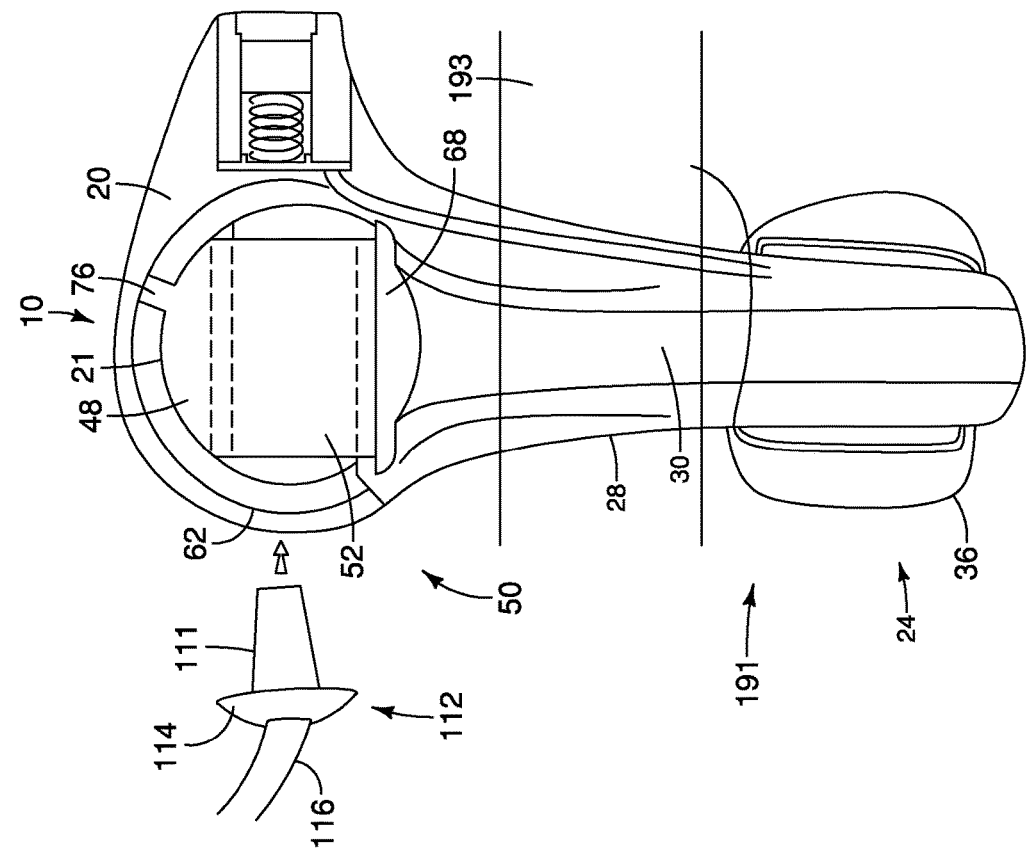

LOW PROFILE GASTROSTOMY TUBES

RELATED APPLICATIONS

This application claims the benefit of U.S. Provisional Application No. 61/651,691 filed May 25, 2012, which is incorporated by reference herein in its entirety.

TECHNICAL FIELD

The present invention generally relates to medical devices and in particular, to gastrostomy feeding devices having valves to control flow through the devices.

BACKGROUND

Gastrostomy feeding ports provide access to the stomach at a stoma site. The feeding ports are typically left in place over a prolonged period of time and are used for feeding and medicating the patient over this period. Many feeding tubes are provided having a low profile on the external portion for patient comfort and to facilitate activity of the patient. Some of these devices include check valves to prevent the reflux of gastric contents through the port because the leakage of gastric contents, which is highly acidic, can cause severe skin burns or tissue maceration leading to chronic skin infections. Valves, such as duckbill valves, are currently used to prevent food or stomach reflux from exiting the tube through the port and to keep the feeding port clean. One problem with the duckbill valve is that after repeated usage of the duckbill valve and exposure to the stomach acids, the duckbill valve allows stomach acids and other fluids to leak from the valve. Another problem that can occur with the commonly used gastrostomy feeding ports is that thicker fluids may clog the device so that a wider feeding tube and greater external profile are required.

What is needed is a feeding tube that allows for multiple uses while maintaining a leak-proof seal for the stomach contents and other fluids. A feeding tube having a low profile and yet allowing for a larger feeding tube is also desirable.

BRIEF SUMMARY

Accordingly, it is an object of the present invention to provide a device and a method having features that resolve or improve on the above-described drawbacks.

Devices and systems for delivering nutrients to a patient are provided. The gastrostomy feeding device includes a device housing having a proximal portion having an opening therein, a channel operably connected to the opening in the proximal portion, a distal portion having an opening therein, a lumen operably connected to the opening in the distal portion, and a cavity formed within the device housing. The device also includes a rotatable member positioned completely within the cavity and that is rotatable within the cavity relative to the housing. The rotatable member includes a first opening and a second opening and a lumen extending therebetween. The rotatable member is rotatable from a closed configuration to an open configuration where the second opening of the rotatable member is operably connected to the lumen of the device housing. The device further includes an expandable member positioned on the distal portion.

In another aspect, a method for delivering nutrients to a patient is provided. The method includes delivering a distal portion and an expandable member connected thereto of a housing of a gastrostomy feeding device through a stoma and positioning the distal portion within the body cavity. The method further includes expanding the expandable member within the body cavity, inserting a distal end of a connector into an opening in a proximal portion of the device housing and into a first opening of a rotatable member positioned completely within a cavity defined in the device housing. The method includes moving a portion of the connector into a channel of the housing to rotate the rotatable member from a closed configuration to an open configuration, where, in the open configuration a second opening of the rotatable member is operably connected to a lumen in the distal portion of the housing positioned within the body cavity and flowing nutrients through the connector, the second opening and the lumen of the housing and into the body cavity

BRIEF DESCRIPTION OF THE DRAWINGS

FIG. 2 is a side sectional view of the device shown in FIG. 1;

FIG. 3 is a top view of the device shown in FIG. 1;

FIG. 4 is a partial side sectional view of an embodiment of a device in a closed configuration;

FIG. 5 is a partial side sectional view of an embodiment of a device in an open configuration;

FIG. 6 is a partial end view of an embodiment of a gastrostomy feeding device in accordance with the present invention;

FIG. 7 is a partial side view of the embodiment shown in FIG. 6;

FIGS. 11A-11C illustrate operation of an embodiment of a device in accordance with the present invention.

DETAILED DESCRIPTION

Figure 1:
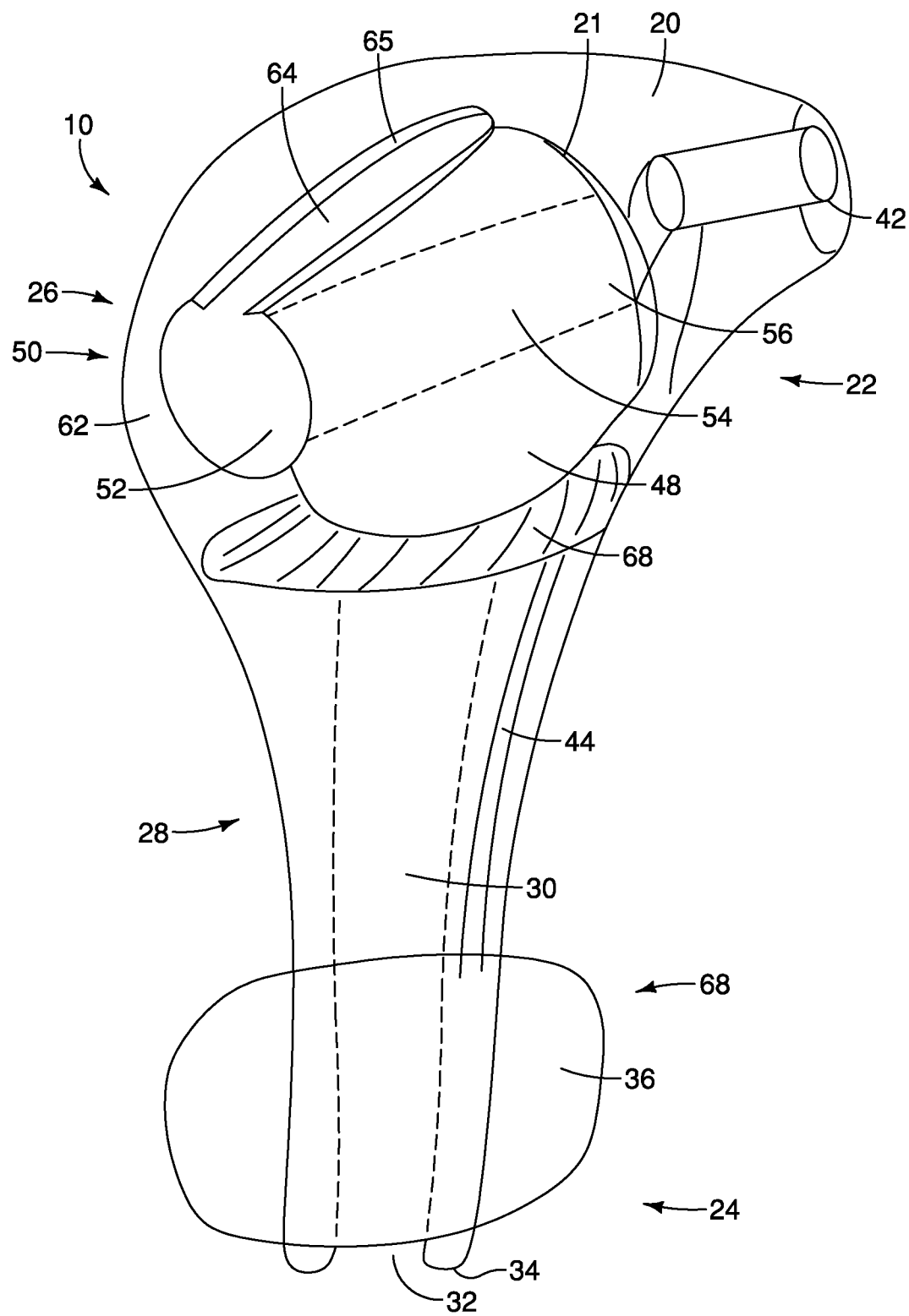
FIG. 1 is a perspective view of an embodiment of a gastrostomy feeding device in accordance with the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the gastrostomy tube device to a patient. Hence the term "distal" means the portion of the gastrostomy tube device that is farthest from the physician and the term "proximal" means the portion of the gastrostomy tube device that is nearest to the physician.

FIG. 1 illustrates a gastrostomy tube device 10 in accordance with an embodiment of the present invention. The device 10 includes a housing 20 having a proximal portion 22 and a distal portion 24. The proximal portion 22 includes a valve 26 that is configured to remain external to a body cavity. The distal portion 24 includes a tubular portion 28 having a lumen 30 extending therethrough. The tubular portion 28 includes an opening 32 configured to connect the lumen 30 to the body cavity, for example for delivering nutrients through the lumen 30.

The device 10 also includes an expandable member 36 is positioned near a distal end 34 of the tubular portion 28. The expandable member 36 may be provided to hold the device 10 in position within the body cavity as explained in more detail below. The expandable member 36 may be a balloon as shown in FIG. 1 that is connected to and surrounds the tubular member 28. When expanded, the expandable member 36 may also provide a seal against a wall within the body cavity. In some embodiments, the expandable member 36 may be a mechanically expandable portion such as a mesh that expands against body cavity. Other types of expandable members may also be used. As shown in FIG. 1, the proximal portion 22 of the device 10 includes a port 42 that operably connects to the expandable member 36. For example, when the expandable member 36 is provided as a balloon, the port 42 is an inflation port having a lumen 44 connected between the port 42 and the expandable member 36 so that the expandable member 36 may be inflated once the device 10 is in proper position. The expandable member 36 is shown in an expanded configuration 68 in FIG. 1.

The valve 26 of the device 10 includes a rotatable member 48 enclosed within a cavity 21 formed in the housing 20 and movable relative to the housing 20. The rotatable member 48 may be completely enclosed within the housing 20. In some embodiments, the rotatable member 48 may be moved by insertion of an object such as a feeding tube or a syringe into the rotatable member 48 as described below. The rotatable member 48 may be provided as a spherical ball valve as shown in FIG. 1. The cavity 21 may be sized and shaped closely hold the rotatable member 48 and to allow the rotatable member 48 to rotate within the cavity. In some embodiments, the rotatable member 48 may be spherical, cylindrical or ellipsoid, although other shapes may also be used. The valve 26 has a closed configuration 50 shown in FIG. 1 where access from outside of the device 10 to the body cavity is prevented. The rotatable member 48 includes a first opening 52 connected to a lumen 54 extending through the rotatable member 48. A second opening 56 is also connected to the lumen 54 and operably connects to the lumen 30 when the rotatable member 48 is moved to an open configuration 60 described below and as shown in FIG. 5. The valve 26 may be made from any material known to one skilled in the art that can withstand caustic substances like stomach acids. By way of non-limiting example, the valve 26 may be made from a durable polymer material, such as TEFLON or DELRIN.

As shown in FIG. 1, the housing 20 of the device 10 may include an opening 62 connected to a channel 64 formed in the housing 20. The channel 64 extends through a wall 65 of the housing 20 from cavity 21 to the outside of the housing 20. The opening 62 of the housing 20 aligns with the first opening 52 of the rotatable member 48 in the closed configuration 50. The opening is sized to receive a distal portion of a connector such as a feeding tube or syringe for delivering nutrients to the patient as shown and described below. A seal 68 may also be provided in the housing 20 to prevent contents from the body cavity from exiting through the valve 26. The seal may be any kind of seal known to one skilled in the art that can withstand caustic substances like stomach acids. By way of non-limiting example, the seal 68 may be formed of silicone, polyisoprene or thermoplastic elastomer and may be provided as a disc, a washer or an o-ring that is positioned beneath the rotatable member 48 to provide a seal against caustic materials.

FIG. 2 illustrates the device 10 in the closed configuration 50. The expandable member 36 is in a collapsed configuration 70 where the expandable member is positioned against the tubular portion 28 and having a low profile that allows the distal portion 24 to be inserted through a stoma and into the patient's body cavity. An inflation valve 74 is shown in the port 42 for inflating the expandable member 36 once the distal portion 24 of the device 10 is positioned within the body cavity.

FIG. 2 also illustrates an embodiment of the device 10 including a guide member 76 that extends outward from a surface 78 of the rotatable member 48. The guide member 76 is provided to control the movement of the rotatable member 48. In some embodiments, the guide member 76 is movable within a guide channel 82 that is formed in the housing 20. The guide channel 82 may be enclosed within the housing 20 and extend from the cavity 21. In some embodiments, the guide channel 82 may be sized and shaped to mate with the guide member 76 to limit the lateral and longitudinal movement of the guide member 76 and thus the movement of the rotatable member 48. In some embodiments, the guide channel 82 may have a width slightly larger than the guide member 76 and a length that allows the guide member to move between about 50 to 100° about the circumference of the cavity 21. In some embodiments, the rotation is between about 60 to 90°. The degree of rotation will be determined by the positioning of the openings 52, 56 in the rotatable member 48 and the position of the opening 62 and the lumen 30 in the housing 20. For example, the degree of rotation permitted will vary if the openings 52, 54 are other than opposite each other on the circumference of the rotatable member 48 or the position of the housing opening 62 relative to the lumen 30 is changed. Additional degrees of rotation may also be used and will depend on the positioning of the openings of the housing and the rotatable member. The guide channel 82 may have a length that allows the rotatable member to from the closed configuration 50 to the opening configuration 60. In some embodiments, the channel 64 may alone control the rotational movement of the rotatable member 48. FIG. 3 illustrates a top view of the device 10 showing the channel 64 extending to the outside of housing 20 and the guide channel 82 within the housing and extending from the cavity 21.

FIG. 4 illustrates the device 10 in the closed configuration 50 and FIG. 5 illustrates the device 10 in the open configuration 60. As shown in FIG. 4, the first opening 52 of the rotatable member 48 is aligned with the opening 62 of the housing 20 in the closed configuration 50. The second opening 56 of the rotatable member 48 is not connected to the lumen 30 of the tubular portion 28. The guide member 76 extends in to the guide channel 82 and is in a first position 87 relative to the housing 20. As shown in FIG. 5, the guide member 76 is in a second position 89 relative to the housing 20 and the second opening 56 in the rotatable member 48 is operably connected to the lumen 30 of the tubular portion 28. The lumen 54 of the rotatable member 48 has been moved from substantially horizontal relative to the lumen 30 of the housing 20 to substantially parallel to the lumen 30. (Compare FIGS. 4 and 5.) The guide member 76 has moved about 80-100° within the guide channel 82 and is stopped from moving farther by the end of the guide channel 82. In some embodiments, the guide member 76 moves about 85-95° within the guide channel 82. The length of the guide channel 82 and the position of the guide member 76 on the rotatable member 48 relative to the first and second openings 52, 56 may be used to limit the rotation of the rotatable member 48 past the point where the opening 56 of the lumen 54 is aligned with the lumen 30 of the tubular member 28. The rotatable member 48 may be rotated from the closed configuration 50 to the open configuration 60 and back to the closed configuration 50.

FIGS. 6 and 7 illustrate an embodiment of a gastrostomy feeding device 110 having a cylindrically shaped rotatable member 148. FIG. 6 illustrates an end view of the device 110 showing a device housing 120 having a tube shaped cavity 121 to house the cylindrical rotatable member 148. FIG. 7 illustrates a side sectional view of the device 110. The device 110 is similar to the device 10 except that the rotatable member is cylindrically shaped rather than spherically shaped. Since the cavity 121 is tubular to closely surround the rotatable member 148, a guide member is not needed to limit the lateral rotation of the rotatable member. The rotation of the rotatable member 148 may be controlled by the length of a channel 164 formed in the housing 120. Similar to the embodiments described above, the housing 120 includes an opening 162 that may be sized and shaped to receive a distal portion of a connector such as a feeding tube or syringe. The opening 162 is aligned with a first opening 152 in the rotatable member 148 in the closed configuration 50. A lumen 154 extends from the first opening 152 to a second opening 156. Similar to the other embodiments described herein, the device 110 may be moved to an open configuration by rotation of the rotatable member. The rotation of the rotatable member 148 may be limited to between about 60 to 90° about the circumference of the cavity 121. The degree of rotation will be determined by the positioning of the openings 152, 156 in the rotatable member 148 and the position of the opening 162 and the lumen 130 in the housing 120. For example, the degree of rotation permitted will vary if the openings 152, 154 are other than opposite each other on the circumference of the rotatable member or the position of the housing opening 162 relative to the lumen 130 is changed. Additional degrees of rotation may also be used and will depend on the positioning of the openings of the housing and the rotatable member. The embodiment of the device 110 may include additional features described with reference to the other embodiments herein.

Figure 8:
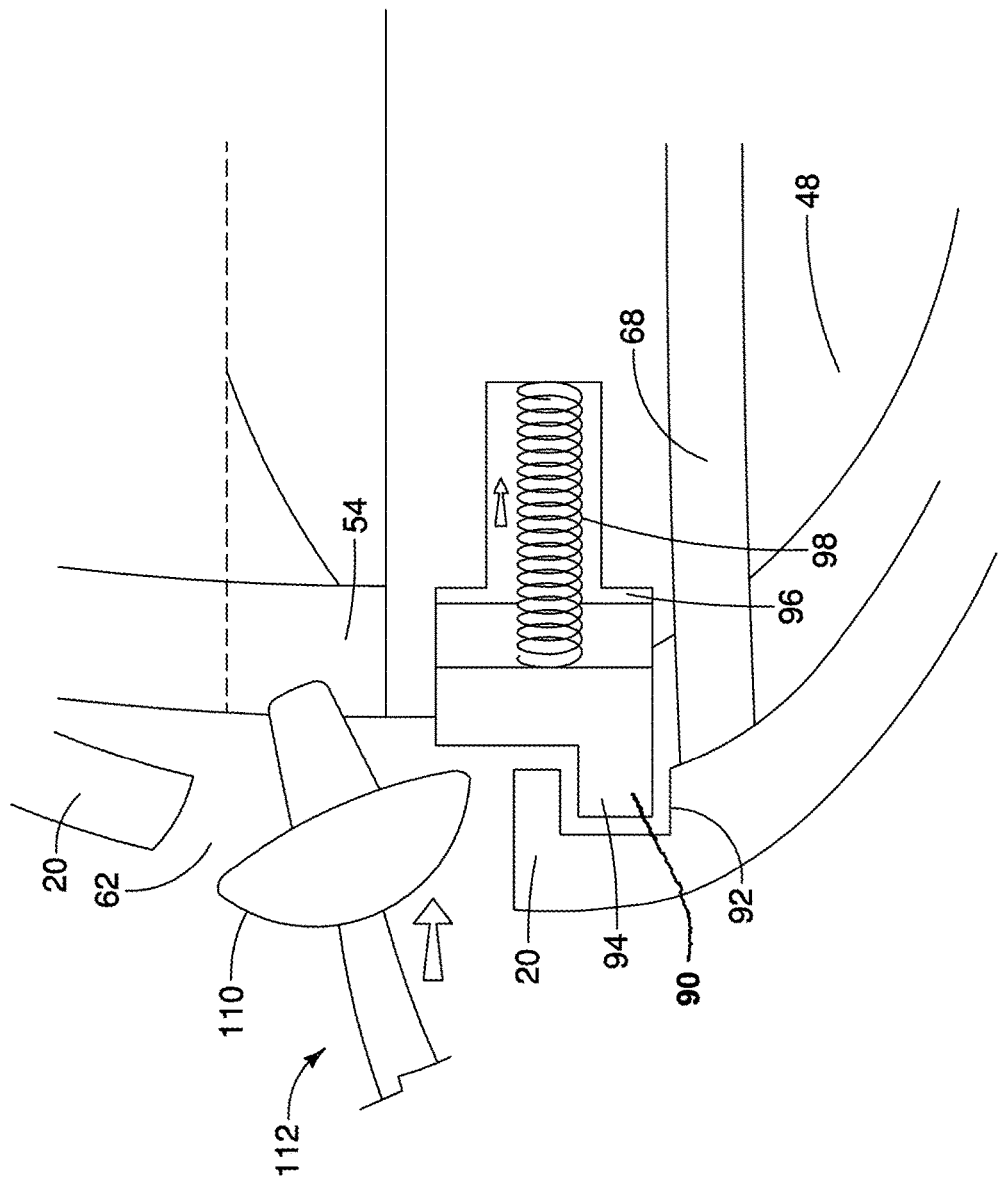
FIG. 8 is a partial sectional view of an embodiment of a gastrostomy feeding device having a lock.

In some embodiments, a locking member 90 may be provided to lock the device in the closed configuration 50 in the absence of a connector. As shown in FIG. 8, the locking member 90 may be provided to lock the rotatable member 48 in position relative to the housing 20. The housing 20 of the device 10 may include an internal recess 92 that is sized and shaped to receive a protrusion 94 of the locking member 90. The rotatable member 48 may also include a recess 96 sized and shaped to receive the locking member 90. The recess 96 may also house a spring 98 that when compressed, allows the rotatable member 48 to move relative to the housing 20. As shown in FIG. 8, a distal portion 110 of a feeding tube or a syringe 112 may be inserted into the opening 62 in the housing 20 to release the locking member. As the distal portion is inserted into the opening 62 of the housing and the lumen 54 of the rotatable member 48, the locking member is moved into the recess 96 in the rotatable member 48 and the spring 98 is compressed. The protrusion 94 of the locking member 90 is moved into the recess 96 so that the protrusion 94 is withdrawn from the recess 92 of the housing 20 and the rotatable member 48 is movable relative to the housing 20.

Figure 9:
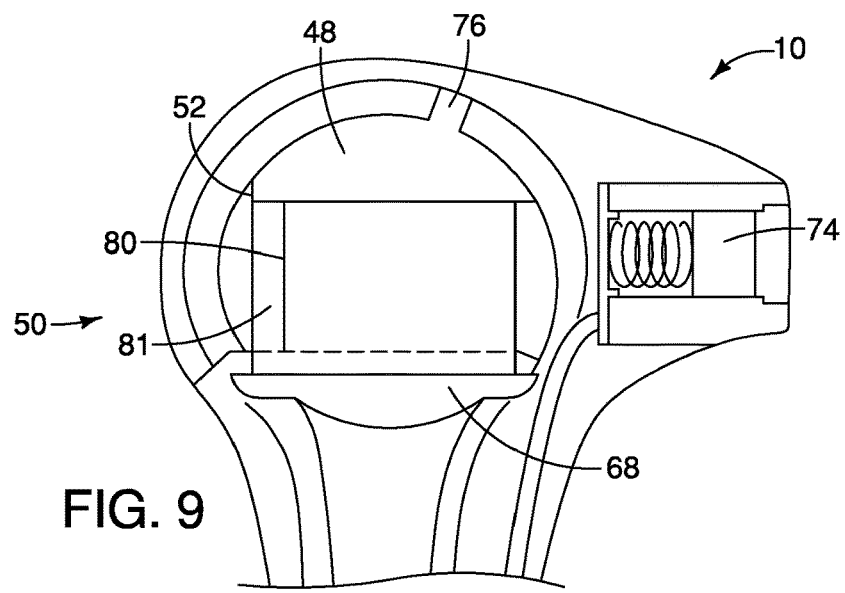
FIG. 9 is a partial side view of an embodiment of a gastrostomy feeding device having a valve.

In some embodiments, the device 10 may include a valve 80 positioned at the first opening 52 of the rotatable member 48 as shown in FIG. 9. By way of non-limiting example, the valve 80 may be made of silicone or other flexible material that covers the opening 52 to keep the lumen 54 free from dirt and other particles when the device 10 is in the closed configuration 50. The valve 80 may include a slit 81 so that the distal portion 110 of the feeding tube 112 can enter the valve 80 and the device 10 may be used as described herein.

Figure 10:
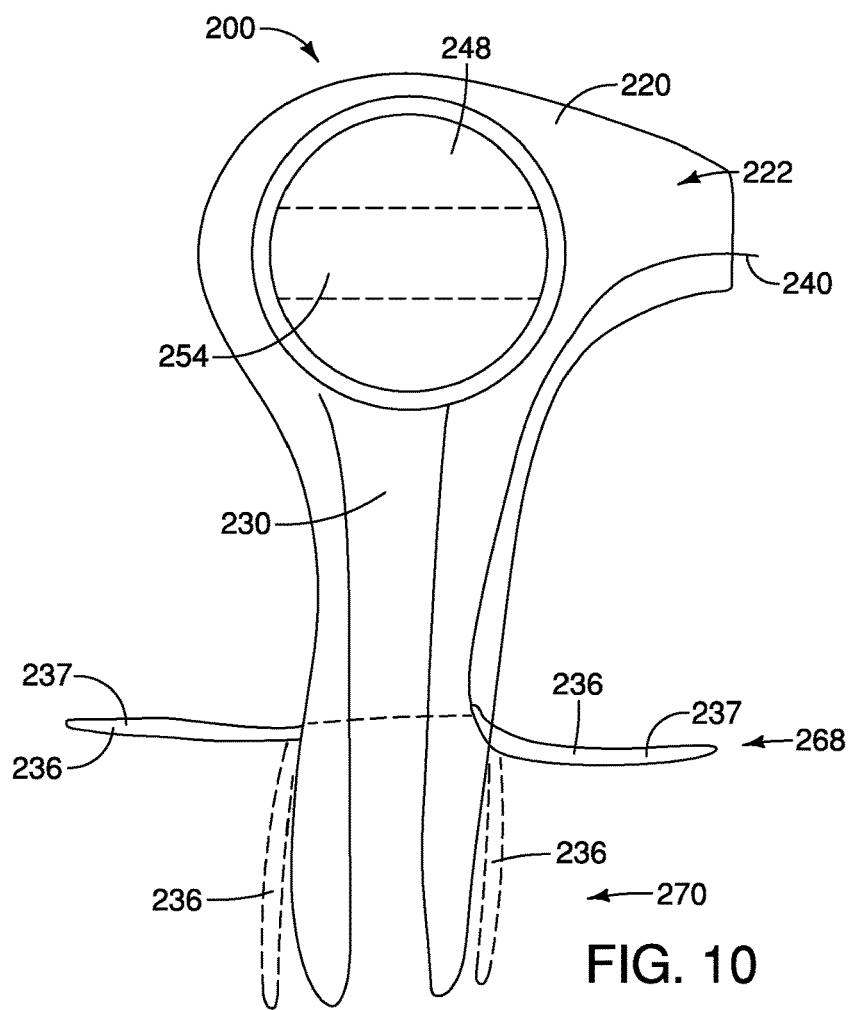
FIG. 10 is a side view of an embodiment of a gastrostomy feeding device in accordance with the present invention.

FIG. 10 illustrates an alternative embodiment of a gastrostomy tube device 200. The device 200 is similar to the devices described above and may include all the alternative features and also includes an alternative expandable member 236. The expandable member 236 is a mechanically expandable device that is movable between an expanded configuration 268 and a collapsed configuration 270 (shown in dashed lines). In the expanded configuration 268, the expandable member 236 holds the device 200 in position similar to the expandable member 36 by holding the position against the internal wall of the body cavity. The expandable member 236 may be a plurality of separate arms 237 or a unitary device, for example a woven mesh that expands and collapses. Other mechanically expandable members may also be used. The expandable member 236 may be collapsed for insertion through the stoma into the body cavity. The expandable member 236 may be expanded and collapsed by one or more control wires 240 that extend to the proximal portion 222 and connect to the expandable member 236.

FIGS. 11A-11O illustrate operation of an embodiment of the gastrostomy tube device. By way of non-limiting example, the device 10 will be shown although any of the devices described herein may operate similarly. The connector is illustrated using a feeding tube device, although other connector known in the art may also be used. FIGS. 11A-11O illustrate the device 10 in position for use with the patient. The tubular portion 28 has been inserted through a stoma and the distal portion 24 of the device 10 is positioned within a body cavity 191. The proximal portion 22 of the device 10 is positioned external to the patient's skin 191. The expandable member 36 shown as a balloon has been expanded by inflation using the port 42 connected to the lumen 44. The expandable member 36 is expanded to hold the device 10 in position within the body cavity 191.

Figure 11C:
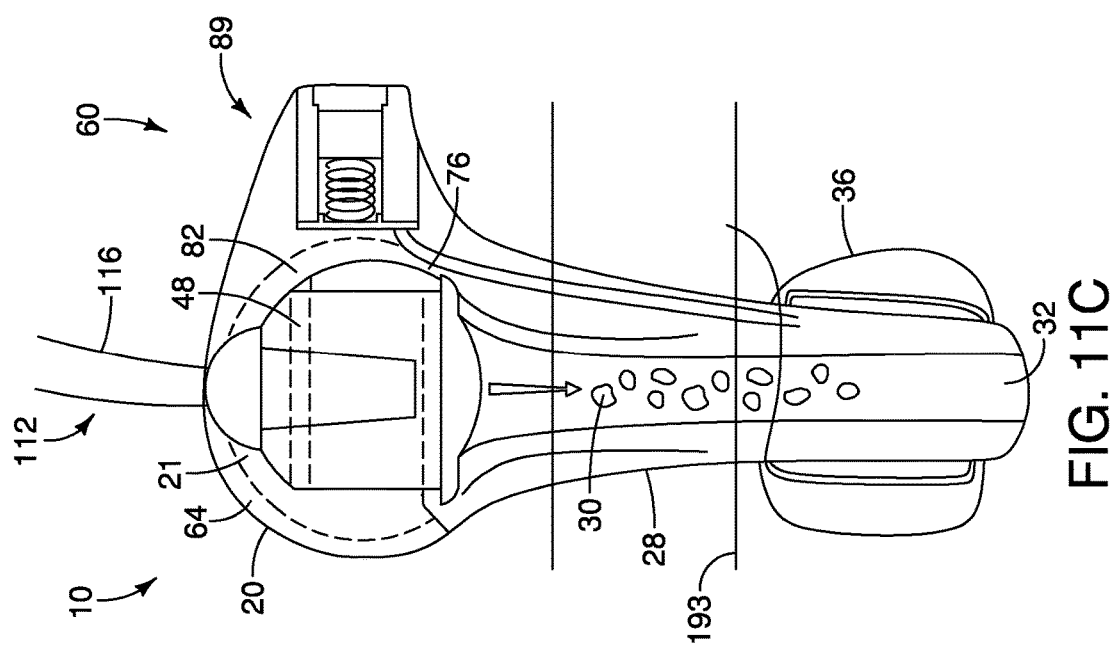

As shown in FIG. 11A, a distal end 111 of a feeding tube 112 is to be inserted into the opening 64 of the housing 20. As discussed above, a syringe may also be used. The distal portion 110 of the feeding tube 112 may also include a flange 114 extending radially away and wider than a tube body 116 or the distal end 111. The opening 62 may be sized and shaped to accommodate the flange 114 as shown in FIG. 1. The opening 62 may be wider than the channel 64 so the channel helps to secure the feeding tube 112 in the housing 20 by movably positioning the flange 114 underneath the housing 20 adjacent to the channel 64 so that the feeding tube 112 is not accidentally released when the device 10 is in the open configuration 60 (see FIG. 11C). The tube body 116 of the feeding tube 112 is sized so that the tube body 116 moves within the channel 64 to rotate the rotatable member 48. The device 10 is in the closed configuration 50 when the feeding tube 112 is connected to the device 10 as shown in FIG. 11A. The distal end 111 of the feeding tube 112 is sized and shaped to be inserted into the first opening 52 of the rotatable member 48.

As shown in FIG. 11B, the distal end 111 of the feeding tube 112 has been inserted into the opening 62 of the housing 20 and into the first opening 52 of the rotatable member 48. The distal end 111 is positioned within the lumen 54 of the rotatable member 48 and a length of the distal end 111 extending distally from the flange 114 is sized to be no longer than a length of the lumen 54 of the rotatable member 48. In some embodiments, the length of the distal end 111 may be shorter than the length of the lumen 54. The flange 114 of the feeding tube 112 fits into the opening 62 of the housing 20 and may be sized so that a perimeter of the flange 114 extends beyond a perimeter of the first opening 52. The flange 114 may act as a stop to prevent the feeding tube 112 from being inserted too far into the lumen 54 and to act as a cover for the first opening 52 to help prevent release of fluids out of the first opening 52. As described above, the flange 114 also helps to secure the feeding tube 112 in the housing 20 so that the feeding tube 112 cannot be removed from the housing 20 when the device 10 is in the open configuration 60. Once the feeding tube 112 is positioned in the device 10, the feeding tube 112 and the rotatable member 48 may be rotated relative to the housing 20.

FIG. 11C illustrates the device 10 in the open configuration 60. The feeding tube 112 positioned within the rotatable member 48 has been moved relative to the housing 20 so that the tube member 116 has advanced into the channel 64 from the opening 62 and the guide member 76 has moved in the guide channel 82 from the first position 87 (shown in FIG. 11B) to the second position 89. The second opening 56 of the rotatable member 48 is aligned with the lumen 30 of the tubular portion 28 so that the lumen 54 of the rotatable member 48 is parallel to the lumen 30. Nutrients 115 may be delivered through the feeding tube 112 into the lumen 30 and out of the opening 32 of the tubular portion 28 into the body cavity 193.

Once the nutrients 115 have been delivered to the body cavity 193, the device 10 may be returned to the closed configuration 50. If desired, the lumen 30 may be rinsed using the feeding tube 112 before closing the connection between the second opening 56 and the lumen 30. To return the device 10 to the closed configuration 50, the tube body 116 is pulled back toward the opening 62 in the housing 20. The rotatable member 48 moves with the feeding tube 112 and rotates within the cavity 21 relative to the housing 20 so that the second opening 56 moves out of alignment with the lumen 30. The guide member 76 moves from the second position 89 to the first position 87 within the guide channel 82 so that the rotation of the rotatable member 48 is along a single axis controlled by the movement of the guide member 76 in the guide channel 82. The length of the guide channel 82 in some embodiments corresponds to the distance the rotatable member 48 moves between the closed configuration 50 and the open configuration 60.

The flange 114 maintains the feeding tube 112 in the housing 20 as the tube body 116 is being moved along the channel 64 toward the opening 62 in the housing 20. Once the guide member 76 reaches the first position 87, the flange 114 is aligned with the opening 62 so that the feeding tube 112 can be removed from the device 10. The lumen 54 of the rotatable member 48 may be rinsed as the feeding tube 112 is removed or with a separate device if desired. The device 10 may remain in the closed configuration 50 until the next nutrient delivery. The seal 68 when present and positioned against the rotatable member 48 helps prevent any body cavity contents from exiting the device 10 in the closed configuration.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A gastrostomy feeding device comprising:
 a device housing comprising:
  a proximal portion having an opening therein;
  a channel operably connected to the opening in the proximal portion;
  a distal portion having an opening therein;
  a lumen operably connected to the opening in the distal portion, and
  a cavity formed within the device housing;
 a rotatable member positioned completely within the cavity and rotatable within the cavity relative to the housing, the rotatable member comprising a first opening and a second opening and a lumen extending therebetween; the rotatable member being rotatable from a closed configuration to an open configuration where the second opening of the rotatable member is operably connected to the lumen of the device housing and at least a portion of the lumen of the device housing adjacent to the opening in the distal portion and the lumen of the rotatable member are parallel in the open configuration;
 a locking member for releasably locking the rotatable member in the closed configuration, the entire locking member positioned internal to an exterior surface of the housing so that a protrusion of the locking member extends into an internal recess located entirely within the device housing in the closed configuration and is movable into a recess in the rotatable member to release the locking member so that the rotatable member is movable relative to the housing; and
 an expandable member positioned on the distal portion.

2. The device of claim 1, wherein the rotation of the rotatable member is between 50 to 100°.

3. The device of claim 1, wherein the rotatable member is spherically shaped.

4. The device of claim 1, wherein the rotatable member is cylindrically shaped.

5. The device of claim 1, wherein the internal recess within an interior portion in the housing is for mating with the protrusion.

6. The device of claim 1, wherein the locking member comprises a spring for urging the locking member into a locked position.

7. The device of claim 1, wherein the device further comprises a valve positioned within the first opening of the rotatable member.

8. The device of claim 1, wherein the rotatable member comprises a guide member on an outer surface of the rotatable member and the housing comprises a guide channel for reception of the guide member therein, the guide member and the guide channel together limiting a movement of the rotatable member in an axial direction and a longitudinal direction.

9. The device of claim 1, wherein the lumen of the rotatable member is horizontal to the lumen of the device housing in the closed configuration and the lumen of the rotatable member is parallel to the lumen of the device housing in the open configuration.

10. The device of claim 1, wherein the device housing comprises a first axis extending perpendicular to a second axis extending parallel to the lumen in the device housing, and wherein the lumen of the rotatable member is rotatable away from the first axis.

11. The device of claim 1, wherein the channel extends through a wall of the device housing from the cavity to an exterior surface of the proximal portion of the device housing.

12. A system for delivering nutrients to a patient, the system comprising:
   a gastrostomy feeding device comprising:
      a device housing comprising a proximal portion having an opening therein, a channel operably connected to the opening in the proximal portion, a distal portion having an opening therein, a lumen operably connected to the opening in the distal portion, and a cavity formed within the device housing;
      a rotatable member positioned completely within the cavity and rotatable within the cavity relative to the housing, the rotatable member comprising a first opening and a second opening and a lumen extending therebetween; the rotatable member being rotatable from a closed configuration to an open configuration where the second opening of the rotatable member is operably connected to the lumen of the device housing and at least a portion of the lumen of the device housing adjacent to the opening in the distal portion and the lumen of the rotatable member are parallel in the open configuration; and
      an expandable member positioned on the distal portion; and
   a connector having a distal end and a flange positioned proximal to the distal end of the connector, the distal end of the connector extendable through the opening in the proximal portion of the device housing into the first opening of the rotatable member so that the flange of the connector releases a locking member and a distal portion of the connector is movable into the channel to rotate the rotatable member from the closed configuration to the open configuration and the connector being configured for delivering the nutrients to the patient.

13. The system of claim 12, wherein the connector comprises a feeding tube or a syringe.

14. The system of claim 12, wherein the channel has a width that is narrower than a diameter of the flange.

15. The system of claim 12, wherein the flange is configured to hold the distal end of the connector within the first opening when the distal portion of the connector is advanced into the channel and a portion of the flange is positioned against the rotatable member and within the housing.

16. The system of claim 12 wherein the expandable member comprises a balloon and the housing includes an inflation port and an inflation lumen operably connected to the balloon.

17. The system of claim 12, wherein the locking member is releasable from a locked configuration by contact with the flange of the connector extended through the opening of the proximal portion of the housing.

* * * * *